United States Patent [19]

Zimmerman

[11] Patent Number: 4,542,291

[45] Date of Patent: Sep. 17, 1985

[54] OPTICAL FLEX SENSOR

[75] Inventor: Thomas G. Zimmerman, Flushing, N.Y.

[73] Assignee: VPL Research Inc., Palo Alto, Calif.

[21] Appl. No.: 428,322

[22] Filed: Sep. 29, 1982

[51] Int. Cl.⁴ .............................................. G01B 5/34
[52] U.S. Cl. ............................. 250/231 R; 250/551; 340/365 R
[58] Field of Search ................. 73/760, 761, 763, 768, 73/774, 775, 800; 340/365 R; 250/231 R, 551

[56] References Cited

U.S. PATENT DOCUMENTS 4,414,537 11/1983 Grimes .......................... 340/365 R Primary Examiner—David C. Nelms
Assistant Examiner—J. Gatto
Attorney, Agent, or Firm—Richard L. Miller

[57] ABSTRACT

An optical flex sensor is provided and consists of a flexible tube having two ends, a reflective interior wall within the flexible tube and a light source placed within one end of the flexible tube and a photosensitive detector placed within the other end of the flexible tube to detect a combination of direct light rays and reflected rays when the flexible tube is bent.

11 Claims, 7 Drawing Figures 4,542,291

OPTICAL FLEX SENSOR

BACKGROUND OF THE INVENTION

The instant invention relates generally to position detectors and more specifically it relates to an optical flex sensor that produces an output signal in response to bending.

SUMMARY OF THE INVENTION

A principal object of the present invention is to provide output signals correlating to the position of corresponding joints.

Another object is to provide an optical flex sensor that is simple, rugged, small and lightweight permitting unhindered, comfortable and natural movement.

An additional object is to provide an optical flex sensor having electrical components that are hermetically sealed making them waterproof and resistant to environmental contaminants.

A further object is to provide an optical flex sensor that uses inexpensive common materials and is assembled either by hand or with simple tools.

A still further object is to provide an optical flex sensor that can be made in a variety of diameters, lengths, materials, and with electrical components that utilize low current and voltage making them safe to use.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The figures in the drawings are briefly described as follows.

DESCRIPTION OF THE PREFERRED EMBODIMENT

Figure 3:
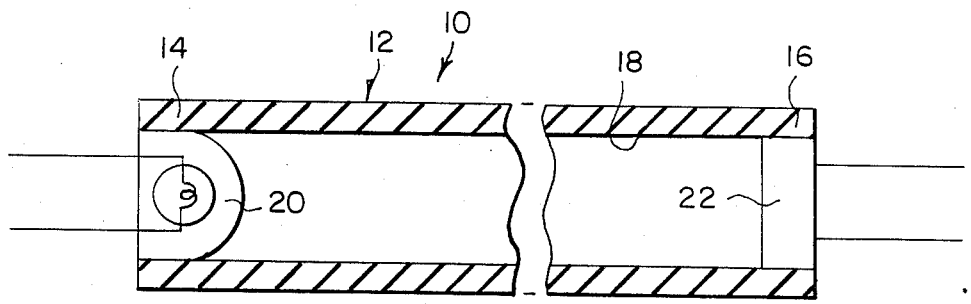
FIG. 3 is a cross sectional view of still another embodiment of the invention.

Turning now descriptively to the drawings, in which similar reference characters denote similar elements throughout the several views, FIG. 3 illustrates an optical flex sensor 10. The sensor 10 consists of a flexible tube 12 that has open ends 14 and 16 a reflective interior wall 18 within the flexible tube 12, a light source 20 placed within end 14 of the flexible tube 12 and a photosensitive detector, or light transmitting device such as an optical fiber 22 is placed within end 16 of the flexible tube 12 so that the intensity of a combination of direct light rays and reflected rays may be detected when the flexible tube 12 is bent.

The flexible tube 10 may be made of black rubber or other suitable material while the interior wall 18 may be coated with aluminum spray paint or other suitable material or in some instants even left untreated.

In its unflexed position the tube 12 is straight. In this position the light emitted from the light source 20 strikes the photosensitive detector 22. As the tube 12 is bent the light received is a combination of direct light rays and reflected rays. The amount of light, reaching the photosensitive detector 22 decreases until a position is reached in which all the light reaching the detector 22 is reflected.

The nature of the photosensitive detector 22 is to change its resistance with light intensity. The combined effect of the bent tube 12 on the light path and the photosensitivity of the detector produces a device that changes its electrical resistance when flexed.

It is to be further appreciated that detector 22 may be a phototransistor, photo silicon controlled rectifier, a photocell, or in the broad sense an optical fiber which carries the signal to another location, or any other of various components which has some output parameter which changes in response to light intensity.

Figure 1:
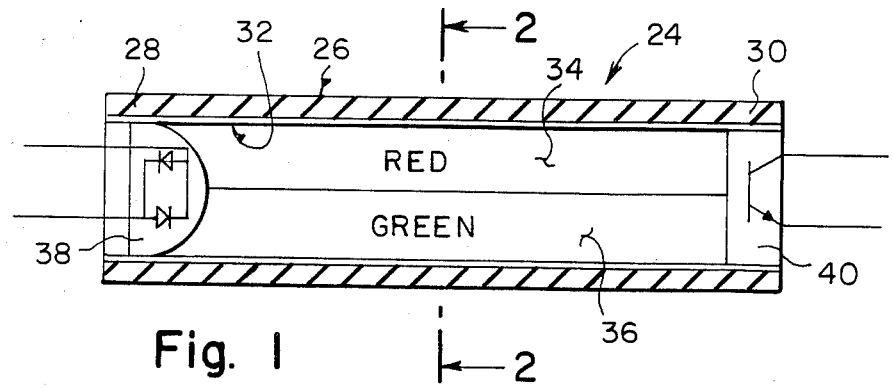
FIG. 1 is a longitudinal cross sectional view of the invention.
Figure 2:
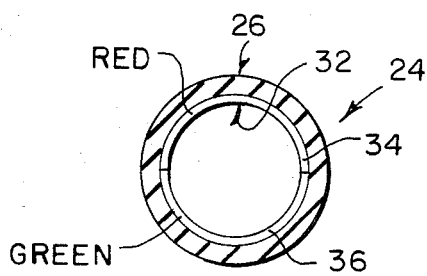
FIG. 2 is a cross sectional view taken along line 2—2 in FIG. 1.

FIGS. 1 and 2 show another embodiment of an optical flex sensor 24. The sensor 24 consists of a flexible tube 26 that has two ends 28 and 30, a reflective interior wall 32 made out of two different longitudinal color areas red 34 and green 36 within the flexible tube 26, a light source 38 that may be either light emitting diodes or infrared emitters and a photosensitive detector 40 that is a silicon phototransistor.

Figure 2A:
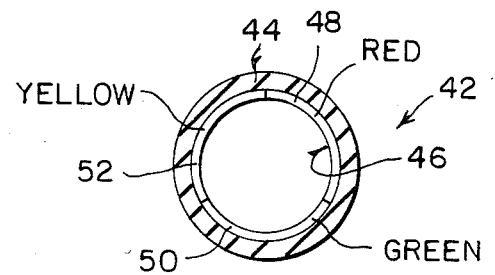
FIG. 2A is a cross sectional view similar to FIG. 2 illustrating another embodiment of the invention.

FIG. 2A shows another embodiment of an optical flex sensor 42. This sensor has within the flexible tube 44 a reflective interior wall 46 made out of three different longitudinal color areas red 40, green 50 and yellow 52. The two different color areas 34 and 36 in the sensor 24 and the three different color areas 48, 50 and 52 in the sensor 42 cause the intensity of light which reaches the photosensitive detector 40 at the opposite end of the tube to be modified according to whether a light source of similar color or different color is reflected from this surface.

In these embodiment the light source 38 would consist of the same multiple number of similar colored sources as there are color wall areas on wall 46 of tube 44. These multiple sources would be pulsed on and off at various intervals of time and the output parameter of detector 40 would accordingly be correspondingly sampled during these time intervals. In this manner the information present would allow one to determine not only the degree that the device is bent but also a direction of bending. It is to be appreciated that the accuracy obtainable of the direction in which the device is bent is increased when a larger number of multiple colored light sources and correspondingly colored walls are employed. Although only the specific case of one, two, and three colors are illustrated in the accompany drawings any number could be chosen and ten for instance would not be an inconceivable number and certainly would permit determining this bending direction with a much higher degree of resolution than three colors would.

In the same way that there is a larger number of suitable photodetector devices which can be utilized for elements 40, and 22, there are also a large variety of light sources which are suitable for element 38, and 20 not to mention just a few such as light emitting diodes, incandescent lamps, in the broad sense an optical fiber carrying light from another source, neon lamps, and other gaseous sources etc.

Figure 4:
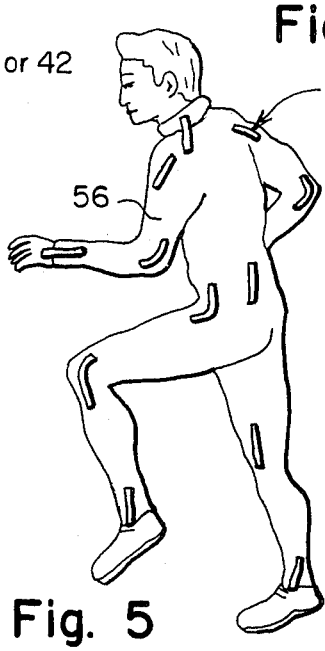
FIG. 4 is a plan view of a glove embodiment of the invention.
Figure 5:
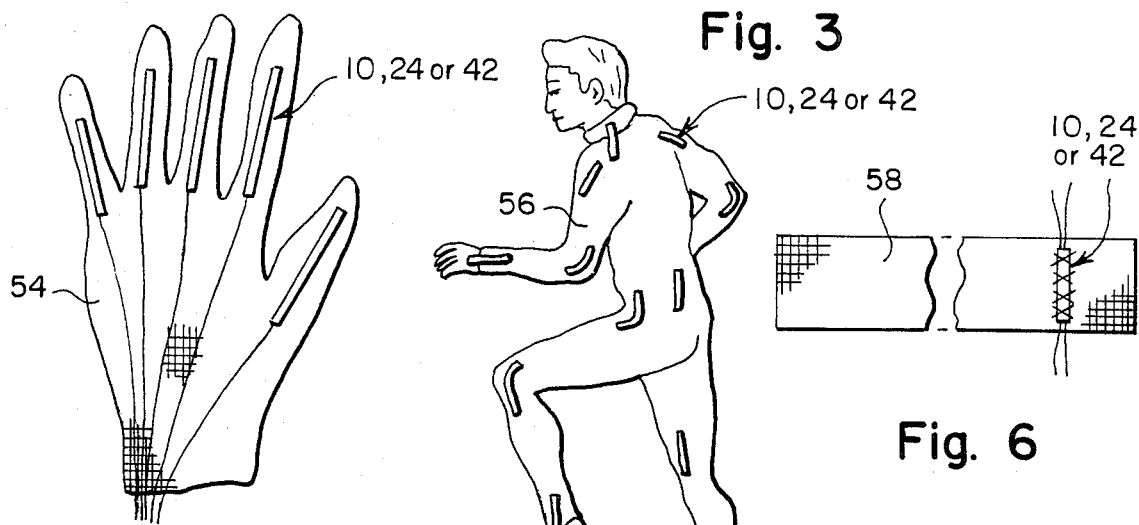
FIG. 5 is a perspective view of a body suit embodiment of the invention.
Figure 6:
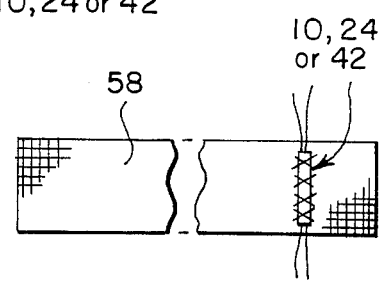
FIG. 6 is a plan view of a elastic bandage embodiment of the invention.

The sensors 10, 24 or 42 can be attached to a fabric of a glove 54 (see FIG. 4), a body suit 56 (see FIG. 5) or an elastic bandage 58 (see FIG. 6) to be placed on appendages of a being or creature to electrically measure the position of joints and limbs, or at least obtain information about their position, velocity, acceleration, etc. or other related parameters.

It is to be further appreciated that sensors 10, 24, and 42 can have their information outputs, and their light source inputs connected by an appropriate network of electrical wires or fiber optical paths (not shown) as required by other design considerations.

The means for securing these sensor may be quite varied depending on their related application they might be sewn, cemented, or other wise inserted in various preexisting tubes etc.

Signals from these sensors can be processed for application in kinesiology, physical therapy, computer animation, remote control and man to machine interface. The optical flex sensors can be used as digital (on/off) or analog switches. The optical flex sensors 10, 24 or 42 may also be used to indicate the bend of mechanical joints or inclination of platforms, as well as a host of other applications too numerous to mention.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An optical flex sensor which comprises:
   (a) fabric;
   (b) a unitary flexible tube component comprising detecting means providing output parameters continuously indicative of the extent of the bending of said tube;
   (c) means for securing said flexible tube to said fabric; and
   (d) means for transmitting said output parameters to an external device whereby said external device can determine when said fabric and secured flexible tube are bent.

2. An optical flex sensor as recited in claim 1 wherein the fabric is the material out of which a garment is made for a living being.

3. An optical flex sensor as recited in claim 1 wherein the means for securing said flexible tube to said fabric is sewing.

4. An optical flex sensor as recited in claim 1 wherein the means for securing said flexible tube to said fabric is cement.

5. An optical flex sensor as recited in claim 1 wherein the means for transmitting said output parameters to an external device is electrical wires.

6. An optical flex sensor as recited in claim 1 wherein the means for transmitting said output parameters to an external device are optical fibers.

7. An optical flex sensor as recited in claim 2 wherein the fabric is the material out of which a garment is made for a being or creature, further comprises a glove with at least one said flexible tube component secured in proximity to at least one joint.

8. An optical flex sensor as recited in claim 2 wherein the fabric is the material out of which a garment is made for a being or creature, further comprises a body suit with at least one said flexible tube component secured in proximity to at least one joint.

9. An optical flex sensor as recited in claim 2 wherein the fabric is elastic material out of which a garment is made for a being or creature, further comprises an elastic bandage with at least one said flexible tube component secured thereto.

10. An optical flex sensor as in claim 1, wherein said flexible tube component comprises an elongated hollow tube having a pair of opposing ends, a light reflective material wall within said tube, at least one light source placed within a first end of said tube, and a photosensitive detector placed within a second end of said tube to detect the intensity of the combination of direct light rays and reflected light rays impinging thereon and producing a continuous output indicative of the extent of bending of the tube component.

11. An optical flex sensor as in claim 10, wherein the reflective interior wall is coated with a plurality of different colored longitudinal areas, and comprising a corresponding plurality of colored light sources, each light source respectively corresponding to a colored area, whereby said detector can detect the direction of bending of the tube component.

* * * * *